United States Patent
Pati et al.

(10) Patent No.: US 10,426,834 B1
(45) Date of Patent: Oct. 1, 2019

(54) METHODS OF STERILIZING DRUGS

(71) Applicant: AKORN, INC., Lake Forest, IL (US)

(72) Inventors: Biswajit Pati, Buffalo Grove, IL (US);
Saeed U. Khan, North Brunswick, NJ (US)

(73) Assignee: AKORN, INC., Lake Forest, IL (US)

( * ) Notice: Subject to any disclaimer, the term of this patent is extended or adjusted under 35 U.S.C. 154(b) by 0 days.

(21) Appl. No.: 15/674,791

(22) Filed: Aug. 11, 2017

Related U.S. Application Data

(60) Provisional application No. 62/373,667, filed on Aug. 11, 2016.

(51) Int. Cl.
*A61K 41/00* (2006.01)
*A61L 2/00* (2006.01)
*A61K 38/12* (2006.01)

(52) U.S. Cl.
CPC .......... *A61K 41/0009* (2013.01); *A61K 38/12* (2013.01); *A61L 2/007* (2013.01); *A61L 2202/21* (2013.01)

(58) Field of Classification Search
CPC ...... A61L 2/007; A61K 38/12; A61K 41/0009
See application file for complete search history.

(56) References Cited

U.S. PATENT DOCUMENTS

2012/0114524 A1* 5/2012 Sigg ...................... A61L 2/0094
422/24

FOREIGN PATENT DOCUMENTS

GB          1411662       * 10/1975

* cited by examiner

*Primary Examiner* — Sean E Conley
(74) *Attorney, Agent, or Firm* — Ron Galant; Polsinelli PC

(57) ABSTRACT

The present invention relates to methods for sterilizing active pharmaceutical ingredients, which may be micronized, using radiation.

11 Claims, No Drawings

METHODS OF STERILIZING DRUGS

FIELD OF THE INVENTION

The present invention relates to methods for sterilizing drugs using radiation. The drugs may be micronized.

BACKGROUND OF THE INVENTION

Active Pharmaceutical Ingredients (APIs) are micronized to break down large particles into smaller particles down to the nanometer range, thus improving dissolution and subsequently improving the efficacy of the API. Micronization is performed on the API in a solid state or as a slurry (that is, an API dispersed in a liquid in the presence of a stabilizer). Solid state micronization has limitations on achieving nano size. Usually, slurry state micronization has the advantage of achieving nano Particle Size Distribution (PSD) due to equipment design and the presence of stabilizers (which insures that micronized particles do not grow back to larger particles). But the process becomes extremely challenging when the micronized API is intended for use in sterile formulations, because neither terminal sterilization nor filter sterilization can be performed. As a result, the typical practice is to receive pre-sterilized API, and then prepare a slurry and perform micronization in a tedious sterile environment. It is particularly challenging to operate micronization equipment in a sterile environment, add the pre-sterile API aseptically, and monitor the micronization process progress in a sterile room.

There are several procedures that are currently used in the industry for sterilization of APIs. The most common methods for sterilizing pharmaceutical ingredients are gamma irradiation and ethylene oxide (EO). Other methods include dry heat and steam (autoclave) sterilization. Gamma irradiation generates an electronic beam that upon contact with the exposed product alters various chemical and molecular bonds, including the reproductive cells of microorganisms, thus destroying living organisms. Gamma radiation is characterized by high penetration, low dose rate, and long dwell time. EO sterilization is a chemical process consisting of four primary variables: gas concentration, humidity, temperature, and time. EO is an alkylating agent that disrupts the DNA of microorganisms, which prevents them from reproducing. The EO penetrates and sterilizes all accessible surfaces of the product to render products sterile by alkylation of proteins essential for cell reproduction. If EO is not completely dissipated, then residual amounts of it remain as a contaminant in the pharmaceutical ingredient. Both gamma irradiation and EO cause pharmaceutical ingredients to degrade, resulting in impurities. And heat-based techniques often cause pharmaceutical ingredients to melt. Accordingly, there is a need in the art for improved methods for sterilizing pharmaceutical ingredients, particularly micronized drugs, and for sterilizing Bacitracin.

SUMMARY OF THE INVENTION

Provided herein is a method of sterilizing Bacitracin, comprising exposing a Bacitracin to E-beam radiation. The radiation dose may be 15-40 kilograys (kGy), 15-25 kGy, or 17.6-25 kGy. The Bacitracin maybe a Bacitracin zinc salt. The Bacitracin may be in solid form, which may be a powder, and may be micronized. After the radiation exposure, the Bacitracin may comprise at least one of the following: not more than 4.5% Impurity-F, not more than 5% early eluting peptides, and not more than 15% total degradants. After radiation exposure, the Bacitracin may also comprise a sum of Bacitracin A, B1, B2, and B3 not less than 80%. After the radiation exposure, the Bacitracin may comprise not more than 4.5% Impurity-F, not more than 5% early eluting peptides, not more than 15% total degradants, and a sum of Bacitracin A, B1, B2, and B3 not less than 80%. After the radiation exposure, the Bacitracin may be characterized by a Sterility Assurance Level of $10^{-6}$.

Further provided herein is a method of sterilizing a micronized API, which comprises exposing a micronized API to radiation. The API may be in the form of a slurry. The radiation may be gamma or E-beam radiation, and may have a dose of 15-40 kGy, 15-25 kGy, or 25-40 kGy. The micronized API may be exposed to the radiation for 240-360 minutes or 208-301 minutes. The micronized API may have a particle size distribution (PSD) of less than or equal to 10 μmm, or less than or equal to 1 nm. The PSD may be an average volume-based PSD.

DETAILED DESCRIPTION

The inventors have discovered that, surprisingly, the process of sterilizing a micronized API can be dramatically simplified by exposing the API to radiation (for example, gamma or E-beam) after the micronization process without significantly increasing API impurities. The sterilization methods described herein avoid the need to pre-sterilize the API, and allow the API to be micronized in a non-sterile environment with non-sterile equipment. A micronized slurry may be stored in a container to maintain sterility after being terminally sterilized by radiation. Subsequently, the sterile micronized API slurry can be added to a product vehicle aseptically. The procedure can be applied to any sterile suspension products in which slurry state micronization is required, where the API is capable of withstanding radiation.

For Bacitracin, there are limited resources available for obtaining a sterilized form as an active pharmaceutical ingredient. Commercially-available sterile Bacitracin is sterilized using aseptic filtration. This and other common approaches to sterilizing pharmaceutical ingredients, including gamma irradiation, EO, and autoclave, all cause significant decreases in the potency and purity of Bacitracin.

The inventors have also discovered that Bacitracin in particular, which may be micronized, can be sufficiently sterilized using E-beam radiation while maintaining potency and minimizing impurities. This may be because of the shorter dwell time of E-beam radiation relative to other forms of radiation such as gamma radiation, which allows for shorter exposure. Shorter exposure allows for rapid dissipation of radiation byproducts which may result in a less severe effect on the physicochemical characteristics of Bacitracin. E-beam radiation is a form of ionizing energy that is generally characterized by its low penetration and high dosage rates, in contrast to the high penetration and low dose rate of gamma radiation. The E-beam is a concentrated, highly charged stream of electrons, and is generated by the acceleration and conversion of electricity. The electrons are generated by equipment referred to as accelerators which are capable of producing beams that are either pulsed or continuous. As the product/material being sterilized passes beneath or in front of the electron beam, energy from the electrons is absorbed. This absorption of energy alters various chemical and biological bonds within the product/material. The energy that is absorbed is referred to as the "absorbed dose." It is this absorption of energy, or "dose delivery," that destroys the reproductive cells of microorganisms by destroying their DNA chains.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

2. Method for Sterilizing a Micronized API

Described herein is a method for sterilizing an API, which may be micronized. The method may comprise exposing the API to radiation. The method may also comprise exposing the API to moist heat or dry heat. The sterilization process may be selected based on the chemical and physical characteristics of the API. If the API is heat-sensitive, then the method preferably comprises exposure to radiation. If the API is heat-stable, then the method may comprise a heat-based sterilization method.

a. API

The API may be an API that can withstand the impact of radiation used in the sterilization method. The API may be nepafenac, fluorometholone, or prednisolone. The API may also be Bacitracin.

The Bacitracin may comprise the following structure and may be represented by the chemical name N-[[2-(1 amino-2-methylbutyl)-4,5-dihydro-4thiazoly]carbonyl]-L-leucyl-D-glutamyl-L-isoleucyl-L-lysyl-D-ornithyl-L-isoleucyl-D-phenylalanyl-L-histidyl-D-aspartyl-L-asparagine cyclic (12→6) peptide. The Bacitracin may be a mixture of related cyclic peptides produced by an organism from the licheniformis group of *Bacillus subtilis*. The Bacitracin may comprise Bacitracin A, B1, B2, and B3, which are known in the art. The Bacitracin may also be a pharmaceutically acceptable salt of a Bacitracin. The salt may be a zinc salt.

The Bacitracin may be in solid form, and may be a powder. The Bacitracin powder may also be micronized. The Bacitracin may have a minimum potency of 65 Units/mg. After being exposed to radiation as described herein, the Bacitracin may have a potency greater than or equal to 65, 66, 67, 68, 69, 70, 71, 72, 73, 74, 75, 76, 77, 78, 79, 80, 81, 82, 83, 84, or 85 Bacitracin Units/mg, or a range thereof. After the radiation exposure, the Bacitracin may also comprise not more than 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, or 2.0% Bacitracin Impurity-F, or a range thereof. After the radiation exposure, the Bacitracin may also comprise not more than 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, or 2.0% early eluting peptides, or a range thereof. After the radiation exposure, the Bacitracin may also comprise not more than 15, 14, 13, 12, 11, 10, 9, 8, 7, 6, or 5% total degradants, or a range thereof. After the radiation exposure, the sum of Bacitracin A, B1, B2, and B3 in the Bacitracin may be not less than 80, 81, 82, 83, 84, 85, 86, 87, 88, 89, 90, 91, 92, 93, 94, or 95%, or a range thereof. The above-described Bacitracin stability levels may be measured by standard testing procedures known in the art, such as those described in the USP monograph for Bacitracin. After the radiation exposure, the Bacitracin may also have a Sterility Assurance Level of $10^{-6}$, or not more than one non-sterile unit for each one million units sterilized.

(1) Micronization

If the API is micronized, then the micronized API may have an average particle size distribution (PSD) of less than or equal to 10 µm, 5 µm, 1 µm, 100 nm, 50 nm, or 10 nm. In particular, the PSD of the micronized API may be less than or equal to 10 µm, which may be suitable for an ophthalmic suspension of the micronized API. The PSD may be measured by laser diffraction analyzer (for example, a MALVERN® particle size analyzer). The PSD measurement may also be based on the inverse relationship between diffraction angle and particle size. The PSD measurement may comprise introducing a dispersion into the path of a collimated laser beam. The dispersion may scatter the laser light to produce a scatter pattern that is captured by an array of optical detectors. The scatter pattern may be deconvoluted by a computer using a Mies theory optical model to generate a volume-based PSD of the sample. The PSD may be an average volume-based PSD.

The micronized API may also comprise nanoparticles of the API, and may have a PSD less than or equal to 1 nM. The PSD may be measured by a laser diffraction analyzer.

The PSD may also be measured by an electron microscope. The electron microscope may allow the shape of the particles to be visualized, and determination of the quality of dispersion, including whether agglomeration of the API is present. The PSD may also be measured by image analysis.

(2) Slurry

The API may be in the form of a slurry or suspension. The slurry or suspension may comprise the API mixed in a liquid medium. The liquid medium may be an aqueous or non-aqueous solvent. The slurry may also contain a surfactant or milling agent that lowers the interfacial tension between liquid and solid, which help solid particles become dispersed in the solvent. The slurry may be contained in a container or a bag, which may be made of low-density polyethylene (LDPE), high-density polyethylene (HDPE), or a colpolymer resin. The container may be a glass vial.

b. Radiation

The API may be exposed to radiation. The radiation may be gamma or electron beam (E-beam). The radiation may bombard the bioburden present in the API, the API slurry, and the container with energy rays, which may destroy the covalent bonds in bacterial DNA. The dosage and time of radiation exposure can be determined by routine and conventional methods known in the art, factoring in the radiation source, type of container, API, characteristics of the API, and the like. The radiation dose may be 5, 10, 15, 20, 25, 30, 35, 40, 45, or 50 kGy, or a range thereof.

If the radiation is gamma radiation, then the dose of radiation may be a low or high dose. The low dose radiation may be 5, 10, 15, 20, or 25 kGy, or a range thereof. The high dose radiation may be 25, 30, 35, 40, 45, or 50 kGy, or a range thereof.

If the radiation is E-beam radiation, then the beams may have an energy of 1, 2, 3, 4, 5, 6, 7, 8, 9, 10, 11, 12, 13, 14, or 15 million electron volts (MeV), or a range thereof. The E-beam radiation may be low or high energy. The low energy may be 1, 2, 3, 4, or 5 MeV, or a range thereof. The high energy may be 6, 7, 8, 9, 10, 11, 12, 13, 14, or 15 MeV, or a range thereof.

The API may also be exposed to multiple cycles of radiation if the API is radiation-stable. The micronized API may be exposed to the radiation for 180, 210, 240, 270, 300, 330, or 360 minutes, or a range thereof, or 208-301 minutes.

The method may comprise exposing the Bacitracin to E-beam radiation. The Bacitracin may be exposed to radiation in a solid form described herein before being formulated, which may be as a pharmaceutical product. The pharmaceutical product may be a Bacitracin ointment, which may comprise 500 Units/g of the Bacitracin. If the API is Bacitracin, then the E-beam radiation dose may be 15, 20, 25, 30, 35, or 40 kGy, or a range thereof, and may be 25 kGy or less, 15-25 kGy or 17.6-25 kGy. The Bacitracin may also be exposed to multiple cycles of radiation.

The present invention has multiple aspects, illustrated by the following non-limiting examples.

Example 1

Sterilization of Bacitracin

This example demonstrates that E-beam irradiation is superior to gamma irradiation, EO, and autoclave sterilization techniques for sterilizing Bacitracin. The sterilization procedures discussed above were utilized to determine the most suitable process for sterilization of the Bacitracin active pharmaceutical ingredient. The objective was to adopt a procedure which has minimum impact on the physical and chemical characteristics of the Bacitracin base material, a process that can produce less degradation of the active drug substance. During evaluation of E-beam irradiation for the purpose of sterilization, product density, size, orientation, and packaging of the material was considered. The irradiation cycle for the sterilization was validated according to AAMI TR33: *Sterilization of health care products—Radiation—Substantiation of a selected sterilization dose—Method VDmax*.

Bacitracin base material was sterilized with Gamma irradiation at a dose range of 22.5 kGy-27.5 kGy. The material was then tested for pre- and post-sterilization samples and the analytical data was evaluated for impact of gamma irradiation. The test results are tabulated in Table 1 below. The data indicate that Bacitracin Impurity-F levels fail to meet USP specifications when gamma sterilization is used, and also a significant drop in the Sum of Bacitracin components. The data also show that a commercially-available Bacitracin API exhibits increased Impurity-F and Early Eluting Peptide levels, and reduced Sum of Bacitracin components, in comparison to pre- and post-micronized non-sterile Bacitracin.

TABLE 1

| RAW MATERIAL | R12-133 | HBN1306201 | HBN130620 | HBN1306201 |
|---|---|---|---|---|
| Origin → | Commercially-available API (XELLIA PHARMA-CEUTICALS) | Pre-micronized (non-sterile) | Micronized (non-sterile) | Gamma Sterilized |
| Bacitracin has a potency of not less than 65 Bacitracin units per mg. | 75.7 | 78.8 | 79.6 | 75.7 |
| Bacitracin Impurity-F: NMT 6.0% | 4.3% | 2.6% | 2.9% | 7.1% |
| Early Eluting Peptides: NMT: 20.0% | 11.5% | 2.7% | 2.8% | 3.8% |
| Total Degradants: NMT: 25.0% | 7.8% | 11.0% | 11.1% | 20.2% |
| Sum of Bacitracin A, B1, B2 and B3: NLT: 70.0% | 80.7% | 86.3% | 86.2% | 76.0% |

The Bacitracin active pharmaceutical ingredient was also sterilized with EO and steam sterilization (autoclave). The analytical data shows a great deal of degradation of the material in both cases as shown in Table 2 below.

TABLE 2

| RAW MATERIAL | HBN1306201 (Non-Radiated) | HBN1306201 EO Sterilized | HBN1306201 Autoclaved |
|---|---|---|---|
| Origin: → | Micronized | Micronized | Micronized-Sterilized |
| Bacitracin has a potency of not less than 65 Bacitracin units per mg. | 78.2 | 41.5 | 12.1 |
| Bacitracin Impurity-F: | 3.5% | 5.6% | 14.5% |

TABLE 2-continued

| RAW MATERIAL | HBN1306201 (Non-Radiated) | HBN1306201 EO Sterilized | HBN1306201 Autoclaved |
|---|---|---|---|
| NMT 6.0% | | | |
| Early Eluting Peptides: NMT: 20.0% | 2.9% | 6.3% | 2.8% |
| Total Degradants: NMT: 25.0% | 10.8% | 44.1% | 66.5% |
| Sum of Bacitracin A, B1, B2 and B3: NLT: 70.0% | 86.3% | 49.6% | 30.8% |

E-Beam radiation was tested at several radiation dose to determine the optimum dose to achieve an sterility assurance of log reduction of $10^{-6}$ with minimum degradation for Bacitracin API. Bacitracin API was sterilized with E-beam radiation doses of 15 kGy, 20 kGy, 25 kGy, 35 kGy, and 40 kGy. The sterilized material was then tested for potency and degradation products. The data obtained are tabulated in Table 3 and Table 4 below.

TABLE 3

| RAW MATERIAL | HBN1307207 (Non-Radiated) | HBN1307207 (Non Radiated) | HBN1307207 (15 kGy) | HBN1307207 (20 kGy) |
|---|---|---|---|---|
| Bacitracin has a potency of not less than 65 Bacitracin units per mg. | 81.0 | 79.6 | 77.0 | 76.3 |
| Bacitracin Impurity-F: NMT 6.0% | 1.9% | 2.0% | 2.2% | 2.0% |
| Early Eluting Peptides: NMT: 20.0% | 2.1% | 3.7% | 3.7% | 3.6% |
| Total Degradants: NMT: 25.0% | <25.0% | 9.6% | 10.4% | 10.2% |
| Sum of Bacitracin A, B1, B2 and B3: NLT: 70.0% | 91.4% | 86.7% | 85.9% | 86.2% |

TABLE 4

| RAW MATERIAL | R13-123 (Non-Radiated) | R13-123 (25 kGy) | R13-123 (35 kGy) | R13-123 (40 kGy) |
|---|---|---|---|---|
| Bacitracin has a potency of not less than 65 Bacitracin units per mg. | 79.0 | 73.9 | 74.4 | 73.7 |
| Bacitracin Impurity-F: NMT 6.0% | 2.0% | 2.6% | 3.1% | 3.5% |
| Early Eluting Peptides: NMT: 20.0% | 3.1% | 3.6% | 4.1% | 4.1% |
| Total Degradants: NMT: 25.0% | 8.6% | 5.9% | 11.0% | 11.4% |
| Sum of Bacitracin A, B1, B2 and B3: NLT: 70.0% | 88.3% | 90.4% | 84.9% | 84.5% |

Particular attention was given to Bacitracin Impurity-F, because the major component of Bacitracin API is Bacitracin A which degrades rapidly into Bacitracin Impurity-F, especially in the aqueous media. The analytical results indicates that the degradation of Bacitracin is higher at the radiation does above 25 kGy.

Based on the evaluation of radiation dose and its impact on physic-chemical characteristics of the Bacitracin API, the E-beam sterilization process was validated with a radiation dose range of minimum 17.6 kGy and maximum 25 kGy.

Bacitracin API was micronized prior to sterilization. The material was tested at pre-micronization, post-micronization and post-sterilization stages. Two lots of Bacitracin API were sterilized as per validated dose of E-beam radiation and tested. The analytical data are tabulated in Table 5 and Table 6 below, meeting the USP specifications.

TABLE 5

| RAW MATERIAL | R14-101 (Non-Sterilized) | R14-101M1 (Non-Sterilized) | R14-101M1S1 (Sterilized) |
|---|---|---|---|
| Origin: → | Non-micronized | Micronized | Micronized-Sterilized |
| Bacitracin has a potency of not less than 65 Bacitracin units per mg. | 77.0 | 75.0 | 76.0 |
| Bacitracin Impurity-F: NMT 6.0% | 1.8% | 1.8% | 4.2% |
| Early Eluting Peptides: NMT: 20.0% | 2.2% | 2.8% | 2.3% |
| Total Degradants: NMT: 25.0% | 8.6% | 8.0% | 13.2% |
| Sum of Bacitracin A, B1, B2 and B3: NLT: 70.0% | 89.0% | 89.0% | 83.0% |

TABLE 6

| RAW MATERIAL | R14-102 (Non-Sterilized) | R14-102M1 (Non-Sterilized) | R14-102M1S1 (Sterilized) |
|---|---|---|---|
| Origin: → | Non-micronized | Micronized | Micronized-Sterilized |
| Bacitracin has a potency of not less than 65 Bacitracin units per mg. | 79.0 | 77.0 | 74.0 |
| Bacitracin Impurity-F: NMT 6.0% | 1.7% | 1.8% | 3.9% |
| Early Eluting Peptides: NMT: 20.0% | 3.6% | 2.6% | 5.0% |
| Total Degradants: NMT: 25.0% | 6.3% | 8.3% | 5.2% |
| Sum of Bacitracin A, B1, B2 and B3: NLT: 70.0% | 90.0% | 89.0% | 83.0% |

Based on the above studies of different modes of sterilization and its impact on the physico-chemical characteristic of Bacitracin, USP, it is evident that E-beam sterilization is the most preferred mode of sterilization as compared to other sterilization techniques.

The invention claimed is:

1. A method of sterilizing Bacitracin, comprising exposing a composition comprising Bacitracin to a dose of 17.6-25 kGy electron-beam (E-beam) radiation, wherein the Bacitracin is a micronized powder, and wherein after the E-beam radiation exposure, the composition comprises not more than 4.5% Impurity-F and is characterized by a Sterility Assurance Level of $10^{-6}$.

2. The method of claim 1, wherein the Bacitracin is a Bacitracin zinc salt.

3. The method of claim 1, wherein after the radiation exposure, the composition comprises not more than 5% early eluting peptides.

4. The method of claim 1, wherein after the radiation exposure, the composition comprises not more than 15% total degradants.

5. The method of claim 1, wherein after the radiation exposure, the composition comprises a sum of Bacitracin A, B1, B2, and B3 not less than 80%.

6. The method of claim 1, wherein after the radiation exposure, the composition comprises not more than 5% early eluting peptides, not more than 15% total degradants, and a sum of Bacitracin A, B1, B2, and B3 not less than 80%.

7. The method of claim 1, wherein the composition is exposed to the radiation for 240-360 minutes.

8. The method of claim 7, wherein the composition is exposed to the radiation for 208-301 minutes.

9. The method of claim 1, wherein the Bacitracin has a particle size distribution (PSD) of less than or equal to 10 µm.

10. The method of claim 9, wherein the PSD is less than or equal to 1 nm.

11. The method of claim 9, wherein the PSD is an average volume-based PSD.

* * * * *